(12) United States Patent
Nuckley et al.

(10) Patent No.: US 9,216,044 B2
(45) Date of Patent: Dec. 22, 2015

(54) STRIPPED PEDICLE SCREW DRIVER BIT

(71) Applicant: Regents of the University of Minnesota, St. Paul, MN (US)

(72) Inventors: David John Nuckley, Minneapolis, MN (US); David Wayne Polly, Jr., Edina, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 431 days.

(21) Appl. No.: 13/646,373

(22) Filed: Oct. 5, 2012

(65) Prior Publication Data

US 2013/0090698 A1 Apr. 11, 2013

Related U.S. Application Data

(60) Provisional application No. 61/544,917, filed on Oct. 7, 2011.

(51) Int. Cl.
*A61B 17/70* (2006.01)
*A61B 17/88* (2006.01)

(52) U.S. Cl.
CPC ......... *A61B 17/7082* (2013.01); *A61B 17/8888* (2013.01)

(58) Field of Classification Search
CPC ........... A61B 17/7082; A61B 17/8886; A61B 17/8888
USPC ..................... 606/99, 104, 300, 301, 305, 308
See application file for complete search history.

(56) References Cited

U.S. PATENT DOCUMENTS

| | | | | |
|---|---|---|---|---|
| 5,941,885 A * | 8/1999 | Jackson | ......................... | 606/104 |
| 6,000,399 A | 12/1999 | Choy | | |
| 6,224,597 B1 | 5/2001 | Coker | | |
| 6,267,025 B1 | 7/2001 | Sand et al. | | |
| 6,324,710 B1 | 12/2001 | Hernandez et al. | | |
| 7,842,044 B2 * | 11/2010 | Runco et al. | ................... | 606/104 |

* cited by examiner

*Primary Examiner* — Anu Ramana
(74) *Attorney, Agent, or Firm* — Shumaker & Sieffert, P.A.

(57) ABSTRACT

A pedicle screw driver bit includes an elongated shank and a head. The shank includes a plurality of threads. The head is connected to one end of and configured to rotate relative to the shank. The head is configured to be received by a tulip connected to a pedicle screw. The threads of the shank are configured to engage a plurality of threads of the tulip such that when the shank is rotated the tulip is drawn into engagement with the head such that the shank, the head, the tulip, and the pedicle screw are substantially prevented from rotating relative to one another.

20 Claims, 3 Drawing Sheets

STRIPPED PEDICLE SCREW DRIVER BIT

This application claims the benefit of application No. 61/544,917, filed Oct. 7, 2011, the entire content of which is incorporated herein by reference.

TECHNICAL FIELD

This disclosure relates to tools and methods employed during spinal surgery.

BACKGROUND

Of the many spinal surgeries performed in the United States each year, pedicle screw fixation is one of the more common surgical techniques used to stabilize the spine for patients with spinal fracture, and degenerative or scoliotic deformities. The effectiveness of pedicle screws is dependent, at least in part, upon the accuracy of their placement. In spite of their effectiveness in the cervical spine, the use of pedicle screws is limited due to the difficulty in placing the screws. The difficulty in placing the screws is accentuated by the flexibility of the cervical spine. Additionally, during placement, the heads of pedicle screws may become stripped, thereby making removal of the screw difficult.

SUMMARY

In general, the following examples are directed to tools and methods for removing or advancing a pedicle screw that has been stripped as it is inserted into a pedicle of a vertebra of a patient during spinal surgery.

In one example, a pedicle screw driver bit includes an elongated shaft and a head. The elongated shank includes a plurality of threads. The head is connected to one end of and configured to rotate relative to the shank. The head is configured to be received by a tulip connected to a pedicle screw. The tulip includes a cylindrical collar that includes a first end and a second end to which an end of the pedicle screw is connected. The threads of the shank are configured to engage a plurality of threads formed on at least one interior surface of the tulip such that when the shank is rotated the tulip is drawn into engagement with the head such that the shank, the head, the tulip, and the pedicle screw are substantially prevented from rotating relative to one another.

In another example, a pedicle screw driver includes a handle, an elongated shaft, and a driver bit. The elongated shaft includes a first end connected to the handle. The driver bit is connected to a second end of the shaft generally opposite the first end. The driver bit includes an elongated shaft and a head. The elongated shank includes a plurality of threads. The head is connected to one end of and configured to rotate relative to the shank. The head is configured to be received by a tulip connected to a pedicle screw. The tulip includes a cylindrical collar that includes a first end and a second end to which an end of the pedicle screw is connected. The threads of the shank are configured to engage a plurality of threads formed on at least one interior surface of the tulip such that when the shank is rotated the tulip is drawn into engagement with the head such that the shank, the head, the tulip, and the pedicle screw are substantially prevented from rotating relative to one another.

In another example, a method includes inserting a pedicle screw driver bit into a tulip connected to a pedicle screw. The driver bit includes an elongated shank including a plurality of threads and a head connected to one end of and configured to rotate relative to the shank. The tulip includes a cylindrical collar that includes a first end and a second end to which an end of the pedicle screw is connected. The method also includes rotating the shank in a first direction to cause the threads of the shank to engage a plurality of threads formed on at least one interior surface of the tulip until the tulip is drawn into engagement with the head of the driver bit such that the shank, the head, the tulip, and the pedicle screw are substantially prevented from rotating relative to one another and rotating the shank in one of the first direction or a second direction opposite the first direction to cause the head, the tulip, and the stripped pedicle screw to rotate together in the one of the first or second direction.

In another example, a kit includes a pedicle screw driver, at least one pedicle screw comprising a tulip, and a stripped pedicle screw driver bit. The stripped pedicle screw driver bit includes an elongated shaft and a head. The elongated shank includes a plurality of threads. The head is connected to one end of and configured to rotate relative to the shank. The head is configured to be received by the tulip of the pedicle screw. The tulip includes a cylindrical collar that includes a first end and a second end to which an end of the pedicle screw is connected. The threads of the shank are configured to engage a plurality of threads formed on at least one interior surface of the tulip such that when the shank is rotated the tulip is drawn into engagement with the head such that the shank, the head, the tulip, and the pedicle screw are substantially prevented from rotating relative to one another.

In another example, a kit includes a plurality of stripped pedicle screw driver bits. Each of the driver bits includes an elongated shaft and a head. The elongated shank includes a plurality of threads. The head is connected to one end of and configured to rotate relative to the shank. The head is configured to be received by a tulip connected to a pedicle screw. The tulip includes a cylindrical collar that includes a first end and a second end to which an end of the pedicle screw is connected. The threads of the shank are configured to engage a plurality of threads formed on at least one interior surface of the tulip such that when the shank is rotated the tulip is drawn into engagement with the head such that the shank, the head, the tulip, and the pedicle screw are substantially prevented from rotating relative to one another. Each of the driver bits is configured to be removably connected to a different type of pedicle screw driver.

The details of one or more examples are set forth in the accompanying drawings and the description below. Other features, objects, and advantages of examples according to this disclosure will be apparent from the description and drawings, and from the claims.

DETAILED DESCRIPTION

Placement of screws into the human spine is a common surgical procedure to allow for a multitude of spinal surgeries to be performed. Pedicle screws, as they are commonly referred to are typically placed into the pedicles of individual vertebra in different regions of the spine, including the cervical, lumbar, and sacral spine. The pedicle screws are driven into a vertebra by a surgeon, typically using a manual driver. The orientation of each screw with respect to the vertebra into which the screw is driven, as well as the spinal column as a whole is an important characteristic of proper pedicle screw placement.

Pedicle screw heads may become stripped during placement due to strong bone and a desire by the implanting physician to apply a very high torque to the screw during insertion into the pedicle. Once a pedicle screw head becomes stripped, it is very difficult with current surgical tools to either advance or remove that screw. One current surgical technique for removing stripped screws involves attaching a rod to the screw tulip and using pliers to twist the rod to either advance or remove the screw. This technique involves a greatly enhanced surgical exposure time. Additionally, this cobbled together apparatus of rod and pliers is not designed for such an application and does not apply reliable torque to the screw.

In view of the foregoing challenges with removing stripped pedicle screws, the following examples illustrate a pedicle screw driver bit that may be employed to remove stripped pedicle screws. Stripped pedicle screw driver bits according to this disclosure may be readily fitted to a wide variety of pedicle screw drivers and are agnostic to pedicle screw head configuration, thus allowing them to be used on any type of pedicle screw head that has been stripped.

Figure 1A:
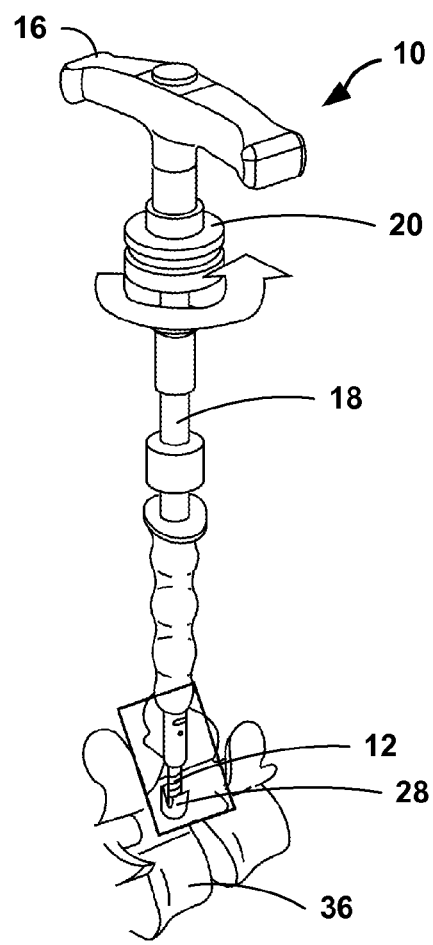
FIG. 1A is schematic illustrations of an example pedicle screw driver including a driver bit in accordance with this disclosure.
Figure 1B:
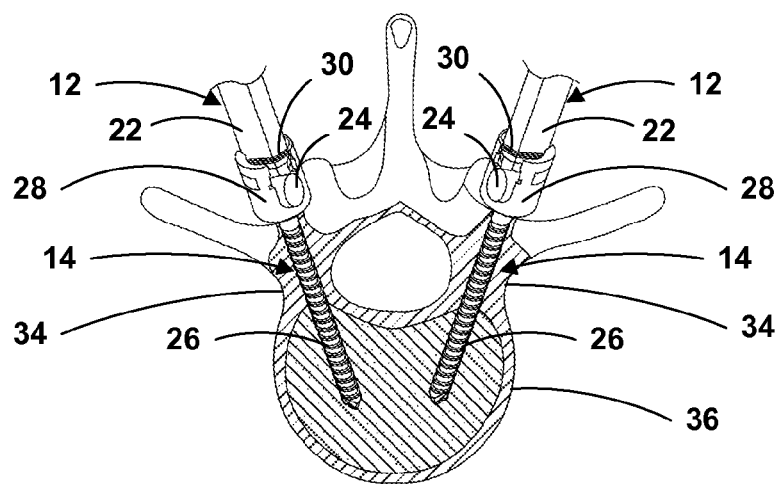
FIG. 1B is an anterior partial section view of a vertebra of a spinal column with two pedicle screws placed therein.

FIGS. 1A and 1B illustrate pedicle screws placed in the pedicles of a vertebra of a patient's spinal column. FIG. 1A is a schematic illustration of example pedicle screw driver 10 including driver bit 12 in accordance with this disclosure. FIG. 1B is an anterior view of a vertebra of a spinal column with two pedicle screws 14 placed therein and engaged by driver bits 12 in accordance with this disclosure.

Figure 2A:
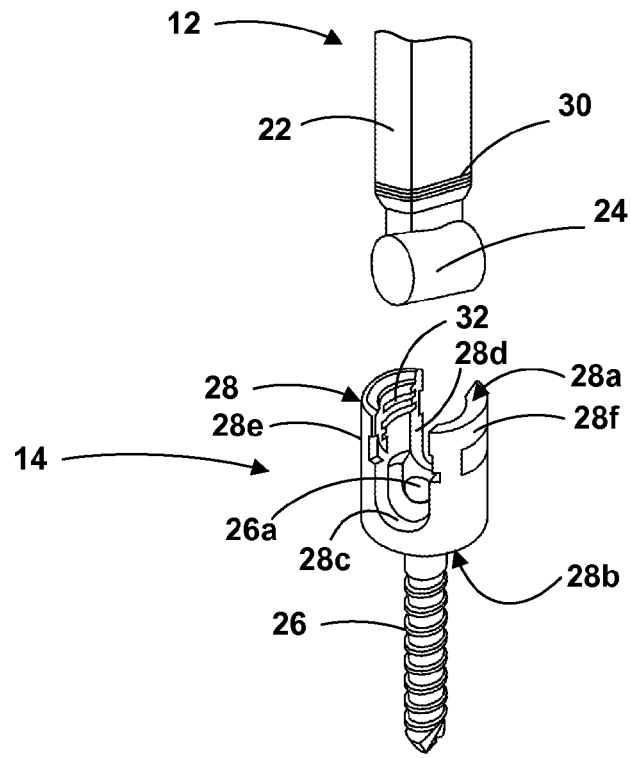
FIGS. 2A and 2B are schematic illustration of a pedicle screw driver bit in accordance with this disclosure engaging a pedicle screw.
Figure 2B:
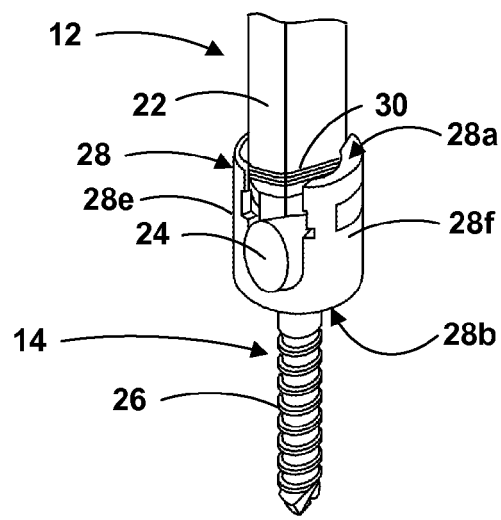

FIGS. 2A and 2B illustrate driver bit 12 as it is inserted into and actuated, e.g. by screw driver 10 of FIG. 1A, to engage pedicle screw 14. FIG. 2A is an exploded view illustrating driver bit 12 prior to insertion into and engagement with pedicle screw 14. FIG. 2A is a perspective view illustrating driver bit 12 in engagement with pedicle screw 14.

Screw driver 10 includes handle 16, shaft 18, and ratcheting mechanism 20. Driver bit 14 includes shank 22 and head 24. Pedicle screw 14 includes screw 26 and tulip 28. Driver bit 12 is connected to shaft 18 of screw driver 10. Driver bit 12 may be configured to be removably connected to a number of types of pedicle screw drivers. For example, shank 22 may include a portion on the opposite end as head 24 that is shaped to be received by a socket at the end of the shaft of the screw driver. In another example, a kit of multiple stripped pedicle driver bits according to this disclosure may be packaged and sold together, in which each of the bits is configured to be removably connected to a different type of pedicle screw driver. Head 24 includes a cylindrical shape including an axis that is generally perpendicular to the longitudinal axis of shank 22. In other words, head 24 is arranged generally transverse to shank 22. Head 24 is a circular cylindrical shape. In another example, however, head 24 may include a rectangular or elliptical cylindrical shape. In any event, head 24 of driver bit 12 is shaped and sized to be received within tulip 28 of pedicle screw 14. Additionally, shank 22 includes threads 30 configured to engage threads 32 in tulip 28. Head 24 is configured to rotate relative to shank 22.

As illustrated in FIGS. 2A and 2B, tulip 28 can be a cylindrical collar that includes open end 28a and end 28b that is connected to screw 26. Screw 26 includes head 26a that is received in and at least partially closes end 28b of tulip 28. Tulip 28 also includes slots 28c and 28d, which extend from open end 28a toward end 28b of tulip 28 and are generally opposing one another around the circumference of tulip 28. Separate walls 28e and 28f of tulip 28 are formed by slots 28c and 28d such that walls 28e and 28f resemble pedals of a tulip. First and second slots 28c and 28d are configured to receive head 24, which may then be rotated to engage walls 28e and 28f of tulip 28.

Pedicle screw 14 is configured to be inserted into the pedicle of a vertebra of the spinal column of a patient during a spinal stabilization surgery, e.g. as illustrated in FIG. 1B in which two pedicle screws 14 are inserted into the pedicles 34 of vertebra 36 of a patient. During such surgeries, a number of pedicle screws are placed in the pedicles of a number of vertebrae and are connected to one another by a rigid rod. Each pedicle screw includes a piece arranged toward the head of the screw that is commonly referred to as a tulip. The tulip receives the spinal stabilization rod ultimately attached to the pedicle screw and includes a mechanism that, when engaged as described below, locks the rod, tulip, and pedicle screw to one another. For example, after inserting the pedicle screws into the pedicles of the patient, the rod is inserted into the tulips of the screws and is locked into place by lock nuts that thread into the tulips over the rods. Before attaching the rods, each of the tulips associated with the pedicle screws may move slightly relative to the respective screw, allowing for some adjustment of the orientation of the rod with respect to the screw. After attaching the rods and securing them with the lock nuts, however, the tulip is drawn into engagement with the rod such that the pedicle screw, tulip, and rod are locked together and the orientation of the tulip and the rod with respect to the pedicle screw is thus fixed. The rod connected to the screws and spanning the multiple vertebrae functions to essentially fuse the vertebrae together and cause them to form one structure, thus stabilizing the region of the spinal column including the vertebrae thus joined.

Pedicle screws are placed with a surgical screw driver that includes a shaft with a head configured to engage the head of the pedicle screw. Pedicle screws are not unlike other screw fasteners in that they may include a variety of screw head configurations configured to be engaged by a variety of screw drivers, including, e.g. slotted, Phillips, Fearson, as well as square, hexagonal, and hexalobular socket (also known as Torx) heads. Pedicle screws may become stripped during placement because the implanting physician applies a torque to the screw head sufficient to cause the screw material to deform and thereby maul the screw head such that it can no longer be engaged by the screw driver with sufficient torque to advance or remove the screw. As noted above, once a pedicle screw head becomes stripped, it is very difficult with current surgical tools to either advance or remove that screw. Driver bit 12 may be employed to remove or advance pedicle screws after the screws have become stripped during surgery, including, e.g. remove or advance pedicle screw 14 illustrated in the example of FIGS. 1A-2B.

Figure 3:
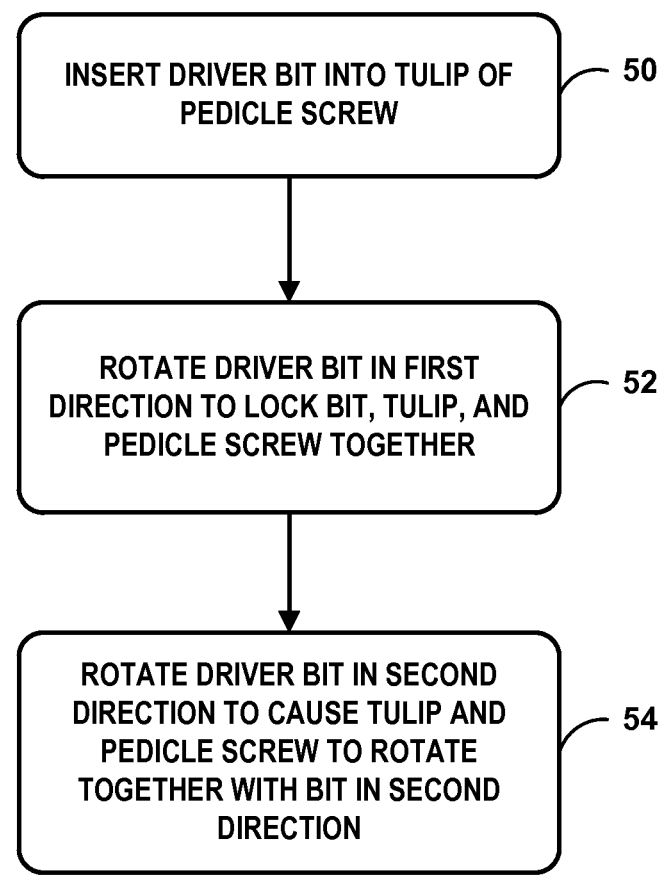
FIG. 3 is a flowchart illustrating an example method of using a pedicle screw driver bit in accordance with this disclosure.

The application of driver bit 12 to remove pedicle screw 14 after it has become stripped is described with reference to the example method of FIG. 3, which includes inserting a pedicle screw driver bit into a tulip of a pedicle screw (50), rotating the bit in a first direction to lock the bit, tulip, and pedicle screw together (52), and rotating the bit in a second direction opposite the first direction to cause the tulip and pedicle screw to rotate together with the bit in the second direction (54). The example method of FIG. 3 is described with reference to example pedicle screw driver 10. However, in other examples, another screw driver configured for receiving driver bit 12 or another pedicle screw driver bit according to this disclosure may be used in conjunction with the techniques described in this disclosure. Additionally, although the method of FIG. 3 is described with reference to using driver bit 12 to remove stripped pedicle screw 14, in another example, driver bit 12 may be employed to advance pedicle screw 14 further into the pedicle of a vertebra of a patient, e.g. further into one of pedicles 34 of vertebra 36 shown in FIG. 1B.

A surgeon working to stabilize a portion of a patient's spinal column, including, e.g. vertebra 36 may strip the head of pedicle screw 14, as described above. In such cases, the surgeon may employ pedicle screw driver 10 with driver bit 12 according to this disclosure to remove stripped pedicle screw 14. Screw driver 10 is configured to be rotated by the surgeon gripping and twisting handle 16, which causes shaft 18 to rotate. Pedicle screw driver bit 12 is configured to be connected to shaft 18, e.g. shank 22 may include a portion on the opposite end as head 24 that is shaped to be received by a socket at the end of shaft 18. Once connected to screw driver 10, driver bit 12 will rotate along with shaft 18 when the surgeon twists handle 16.

As noted above, screw driver 10 includes ratcheting mechanism 20. Ratcheting mechanism 20 may facilitate more efficient driving of pedicle screws engaging shaft 18 to rotate in one direction, e.g. clockwise, with handle 16 when twisted by the surgeon, and to not engage shaft 18 to rotate in a second direction opposite the first, e.g. counter clockwise, with handle 16 when twisted by the surgeon. The direction of rotation that ratcheting mechanism 20 will engage shaft 18 to rotate with handle 16 may be changed, e.g. by triggering an actuator like a button on handle 16.

Once the proper direction rotation for ratcheting mechanism 20 has been selected, the surgeon may position screw driver 10 and driver bit 12 to engage stripped pedicle screw 14. The surgeon may position screw driver 10 with respect to pedicle screw 14 such that a longitudinal axis of screw driver 10 and driver bit 12 is aligned with a longitudinal axis of stripped pedicle screw 14. Screw driver 10 is then lowered such that head 24 of driver bit 12 is received within tulip 28 of pedicle screw 14. In particular, head 24 is received within tulip 28 and slots 28c and 28d thereof. The surgeon continues to lower screw driver 10 such that the end of shank 22 of driver bit 12 including threads 30 begins to also be received by tulip 28 of screw 14.

Driver bit 12 is positioned in tulip 28 of pedicle screw 14 such that threads 30 on shank 22 of screw 14 are arranged to engage threads 32 in tulip 28. The surgeon may then rotate handle 16 in a first direction to cause shaft 18 and shank 22 of driver bit 12 to rotate such that threads 30 on shank 22 are advanced into threads 32 in tulip 28. Once head 24 is received within tulip 28, head 24 is sized and shaped such that the head is unable to rotate within tulip 28. In particular, first and second slots 28c and 28d are configured to receive head 24. Head 24 then engages walls 28e and 28f of tulip 28, which keeps the head stationary within tulip 28. However, head 24 of driver bit 22 is configured to rotate generally freely relative to shank 22 such that head 24 may remain stationary as shank 22 is rotated to cause threads 30 on shank 22 to advance into threads 32 in tulip 28.

The surgeon continues to rotate handle 16 in the first direction to cause threads 30 on shank 22 to advance into threads 32 in tulip 28. As threads 30 on shank 22 engage threads 32 in tulip 28, tulip 28 is drawn into engagement with head 24 such that eventually the surgeon tightens tulip 28 against head 24. The combination of shank 22 including threads 30 engaging threads 32 in tulip 28 and head 24 being received within and engaged by tulip 28 as threads 30 are turned into threads 32 functions in a similar manner as the stabilization rod and lock nuts that are used during spinal stabilization surgeries including pedicle screws, as described above. Just as with the rod and lock nuts described above, after head 24 is received in tulip 28 and threads 30 of shank 22 are turned into threads 32 in tulip 28, tulip 28 is drawn into engagement with head 24 such that pedicle screw 14, tulip 28, head 24, and shank 22 are locked together and are substantially prevented from rotating relative to one another. After engaging tulip 28 of stripped pedicle screw 14 in this manner, the surgeon may twist handle 16 in either direction, e.g. clockwise or counter-clockwise to cause shaft 18 and driver bit 12 to rotate stripped pedicle screw 14, either to advance pedicle screw 14 further into a pedicle of a patient, e.g. one of pedicles 34 in vertebra 36, or to remove pedicle screw 14.

As noted above, driver bit 12 and other pedicle screw driver bits according to this disclosure are agnostic to pedicle screw head configuration. As one example, driver bit 12 is agnostic to the head configuration of pedicle screw 14 because driver bit 12 employ the action of tulip 28 of pedicle screw 14 and not the head of screw 14 to further advance or remove the stripped screw. Thus, driver bits according to this disclosure can be used for any stripped pedicle screws with any head configurations.

Stripped pedicle screw driver bits according to this disclosure, including one or both of the shank and the head of such bits may be manufactured from a variety of materials, including metals such as steel and aluminum or various polymers. In some examples, pedicle screw driver bits may be manufactured from a number of biocompatible materials that resist corrosion and degradation from bodily fluids including, e.g., titanium or stainless steel, or a biologically inert polymer.

Stripped pedicle screw driver bits may be grouped together with other surgical implements as a kit. For example, a pedicle screw surgical kit may include a pedicle screw driver, one or more pedicle screws, and a stripped pedicle screw driver bit according to this disclosure. Such kits may also include one or more of a spinal stabilization rod to connect multiple pedicle screws, a targeting needle, one or more tissue dilators, a bone awl, and calipers for registering distances between pedicle screw heads.

Various examples have been described. These and other examples are within the scope of the following claims.

The invention claimed is:

1. A pedicle screw driver bit comprising:
   an elongated shank comprising a plurality of threads; and
   a head connected to one end of the shank,
   wherein the head is configured to be received by opposing rod-receiving slots of a tulip connected to a pedicle screw,
   wherein the tulip comprises a cylindrical collar that includes a first end and a second end to which an end of the pedicle screw is connected, and
   wherein the threads of the shank are configured to engage a plurality of threads formed on at least one interior surface of the tulip such that when the shank is rotated the tulip is drawn into engagement with the head such that the head is seated in the opposing rod-receiving slots of the tulip, and the shank, the head, the tulip, and the pedicle screw are substantially prevented from rotating relative to one another such that they rotate together as a unit to facilitate rotating the pedicle screw with the pedicle screw driver bit.

2. The driver bit of claim 1, wherein at least one of the shank and the head comprises one of a biocompatible metal or polymer.

3. The driver bit of claim 1, wherein at least one of the shank and the head comprises one of stainless steel, aluminum, or titanium.

4. The driver bit of claim 1, wherein the head comprises a cylindrical shape comprising an axis that is generally perpendicular to the longitudinal axis of the shank.

5. The driver bit of claim 1, wherein the head comprises at least one of a circular, elliptical, or rectangular cylindrical shape.

6. The driver bit of claim 1, wherein the opposing rod-receiving slots of the tulip extend from the first end toward the second end of the tulip.

7. A pedicle screw driver comprising:
a handle;
an elongated shaft comprising a first end connected to the handle;
a driver bit connected to a second end of the shaft generally opposite the first end, wherein the driver bit comprises:
an elongated shank comprising a plurality of threads; and
a head connected to one end of the shank,
wherein the head is configured to be received by opposing rod-receiving slots of a tulip connected to a pedicle screw,
wherein the tulip comprises a cylindrical collar that includes a first end and a second end to which an end of the pedicle screw is connected, and
wherein the threads of the shank are configured to engage a plurality of threads formed on at least one interior surface of the tulip such that when the shank is rotated the tulip is drawn into engagement with the head such that the head is seated in the opposing rod-receiving slots of the tulip, and the shank, the head, the tulip, and the pedicle screw are substantially prevented from rotating relative to one another such that they rotate together as a unit to facilitate rotating the pedicle screw with the pedicle screw driver bit.

8. The pedicle screw driver of claim 7, wherein at least one of the shank and the head comprises one of a metal or polymer.

9. The pedicle screw driver of claim 7, wherein at least one of the shank and the head comprises one of stainless steel, aluminum, or titanium.

10. The pedicle screw driver of claim 7, wherein the head comprises a cylindrical shape comprising an axis that is generally perpendicular to the longitudinal axis of the shank.

11. The pedicle screw driver of claim 7, wherein the head comprises at least one of a circular, elliptical, or rectangular cylindrical shape.

12. The pedicle screw driver of claim 7, wherein the opposing rod-receiving slots of the tulip extend from the first end toward the second end of the tulip.

13. A method comprising:
inserting a pedicle screw driver bit into a tulip connected to a pedicle screw, wherein the driver bit comprises an elongated shank comprising a plurality of threads and a head connected to one end of the shank,
wherein inserting the pedicle screw driver bit into the tulip comprises positioning the head within opposing rod-receiving slots of the tulip, and
wherein the tulip comprises a cylindrical collar that includes a first end and a second end to which an end of the pedicle screw is connected;
rotating the shank in a first direction to cause the threads of the shank to engage a plurality of threads formed on at least one interior surface of the tulip until the tulip is drawn into engagement with the head of the driver bit such that the head is seated in the opposing rod-receiving slots of the tulip, and the shank, the head, the tulip, and the pedicle screw are substantially prevented from rotating relative to one another; and
rotating the shank in one of the first direction or a second direction opposite the first direction to cause the head, the tulip, and the stripped pedicle screw to rotate together in the one of the first or second direction.

14. The method of claim 13, further comprising rotating the shank in the other of the first or second direction to cause the head, the tulip, and the stripped pedicle screw to rotate together in the other of the first or second direction.

15. A kit comprising:
a pedicle screw driver;
at least one pedicle screw comprising a tulip; and
a stripped pedicle screw driver bit comprising:
an elongated shank comprising a plurality of threads; and
a head connected to one end of the shank,
wherein the head is configured to be received by opposing rod-receiving slots of the tulip of the at least one pedicle screw,
wherein the tulip comprises a cylindrical collar that includes a first end and a second end to which an end of the pedicle screw is connected,
wherein the threads of the shank are configured to engage a plurality of threads formed on at least one interior surface of the tulip such that when the shank is rotated the tulip is pulled into engagement with the head such that the head is seated in the opposing rod-receiving slots of the tulip, and the shank, the head, the tulip, and the at least one pedicle screw are substantially prevented from rotating relative to one another such that they rotate together as a unit to facilitate rotating the pedicle screw with the pedicle screw driver bit.

16. The kit of claim 15, wherein at least one of the shank and the head comprises one of a metal or polymer.

17. The kit of claim 15, wherein at least one of the shank and the head comprises one of stainless steel, aluminum, or titanium.

18. The kit of claim 15, wherein the head comprises a cylindrical shape comprising an axis that is generally perpendicular to the longitudinal axis of the shank.

19. The kit of claim 15, wherein the head comprises at least one of a circular, elliptical, or rectangular cylindrical shape.

20. A kit comprising:
a plurality of stripped pedicle screw driver bits, each of the driver bits comprising:
an elongated shank comprising a plurality of threads; and
a head connected to one end of the shank,
wherein the head is configured to be received by opposing rod-receiving slots of a tulip connected to a pedicle screw,
wherein the tulip comprises a cylindrical collar that includes a first end and a second end to which an end of the pedicle screw is connected,
wherein the threads of the shank are configured to engage a plurality of threads formed on at least one interior surface of the tulip such that when the shank is rotated the tulip is drawn into engagement with the head such that the head is seated in the opposing rod-receiving slots of the tulip, and the shank, the head, the tulip, and the pedicle screw are substantially prevented from rotating relative to one another such that they rotate together as a unit to facilitate rotating the pedicle screw with the engaged pedicle screw driver bit, and wherein each of the driver bits is configured to be removably connected to a different type of pedicle screw driver.

* * * * *